United States Patent [19]
Lindow et al.

[11] Patent Number: 5,783,747
[45] Date of Patent: Jul. 21, 1998

[54] FLUID ANALYZING DETECTOR FOR DETECTING THE PRESENCE OF A PARTICULAR ANALYTE IN A FLUID MEDIUM

[75] Inventors: James T. Lindow, Saratoga; Edward R. McCourt, Jr., Palo Alto, both of Calif.

[73] Assignee: Mark Products, Inc., Sunnyvale, Calif.

[21] Appl. No.: 807,070

[22] Filed: Feb. 27, 1997

Related U.S. Application Data

[60] Provisional application No. 60/012,489, Feb. 29, 1996.

[51] Int. Cl.$^6$ .................................................. G01N 15/06
[52] U.S. Cl. ............................ 73/61.41; 73/31.05; 422/92
[58] Field of Search ............................ 73/708, 61.41, 73/61.43, 61.67, 61.71, 61.47, 335.11, 73, 31.05, 23.2; 210/924; 422/69, 88, 92; 436/40, 39

[56] References Cited

U.S. PATENT DOCUMENTS

| | | | |
|---|---|---|---|
| 4,058,802 | 11/1977 | Meyers | 340/224 |
| 4,279,160 | 7/1981 | Fukada et al. | 73/708 |
| 4,782,703 | 11/1988 | Nishi | 73/708 |
| 4,802,370 | 2/1989 | EerNisse et al. | 73/702 |
| 4,861,475 | 8/1989 | Peterson | 210/242.4 |
| 4,890,485 | 1/1990 | Hsu | 73/61.1 R |
| 5,161,415 | 11/1992 | Kodama et al. | 73/708 |
| 5,475,222 | 12/1995 | King | 250/343 |

Primary Examiner—Michael Brock
Assistant Examiner—Jay L. Politzer
Attorney, Agent, or Firm—Robert S. Kelly

[57] ABSTRACT

A rigid cylinder is provided with small perforations to permit the entry of hydrocarbon containing liquids, gases or vapors, and the interior of the cylinder is lined with a sensor material which expands in the presence of hydrocarbons. The interior chamber enclosed by the sensor material is completely filled with an incompressible liquid, and one end of the chamber is sealed by a conventional pressure sensor so that the presence of hydrocarbons causes the sensor material to exert a pressure upon the incompressible liquid to create an output signal in the pressure sensor. A double-chambered device, with only one chamber being perforated and thereby exposed to the hydrocarbons, can be used to compensate the pressure sensor signal for ambient pressure or temperature changes.

18 Claims, 4 Drawing Sheets

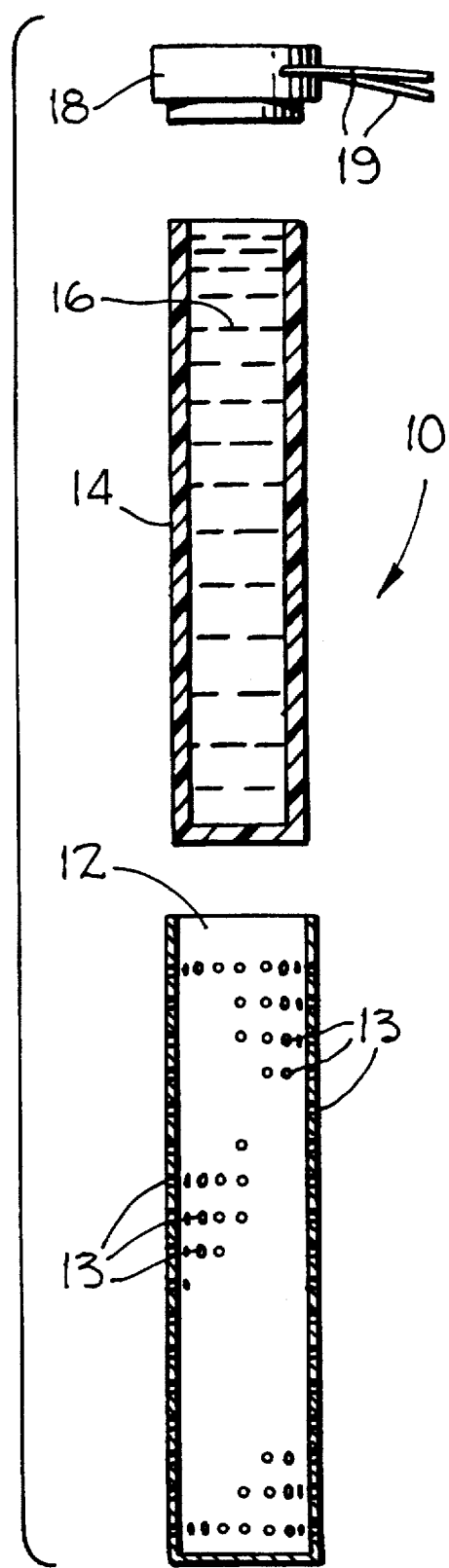

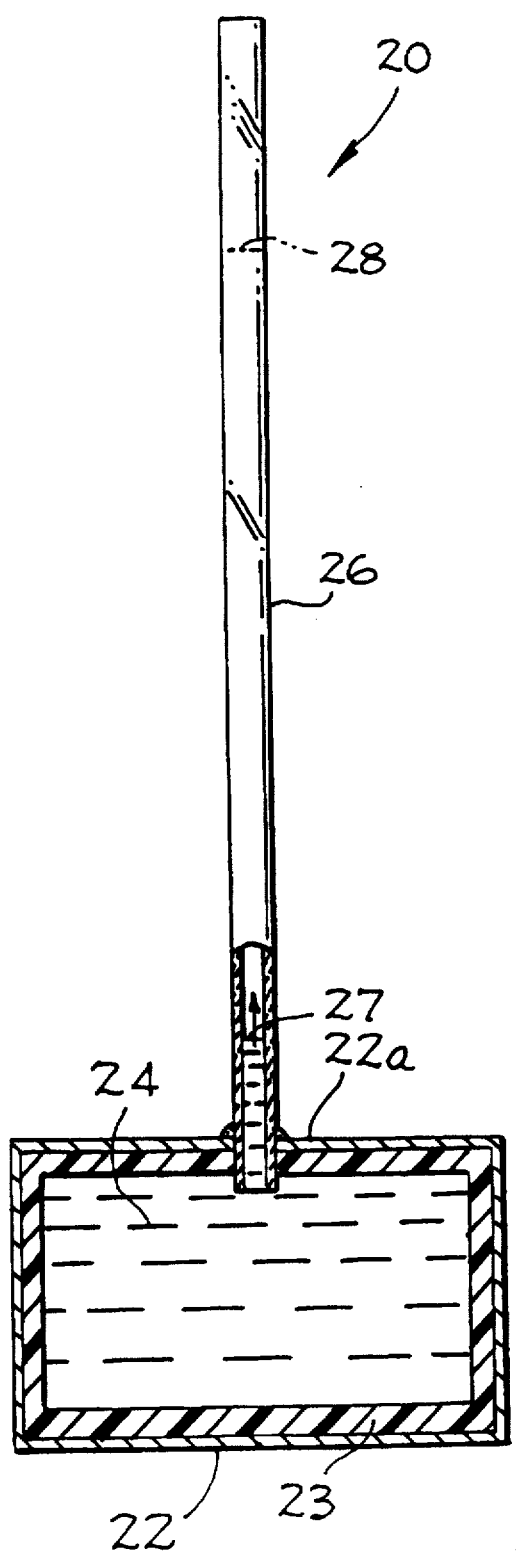

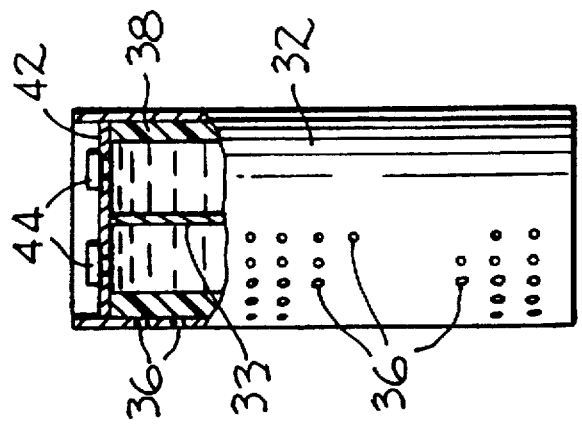
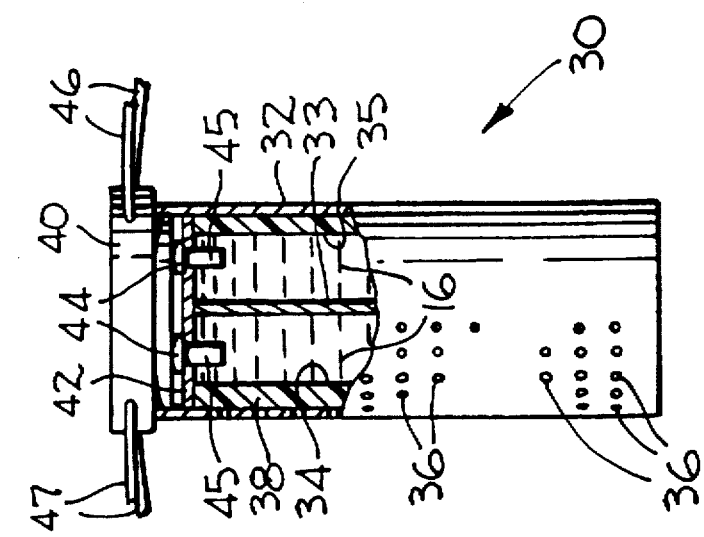

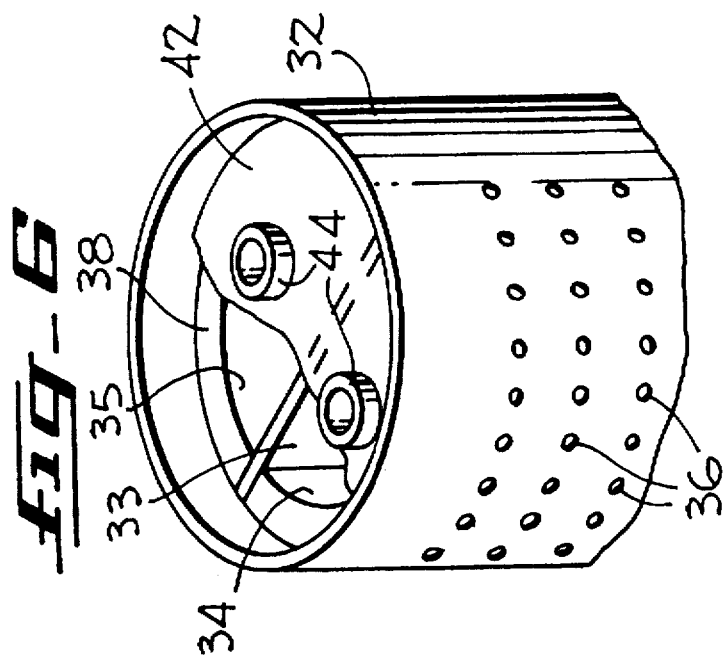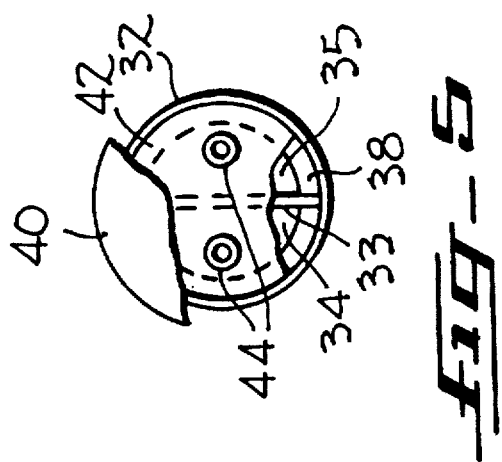

FLUID ANALYZING DETECTOR FOR DETECTING THE PRESENCE OF A PARTICULAR ANALYTE IN A FLUID MEDIUM

REFERENCE TO PRIOR APPLICATION

This application claims the benefit of U.S. Provisional Application No. 60/012,489, filed Feb. 29, 1996 and entitled: HYDROCARBON DETECTOR OF HIGH SENSITIVITY.

BACKGROUND OF THE INVENTION

1. Field of the Invention

The present invention pertains to detectors for detecting the presence of a particular analyte, such as hydrocarbon containing substances in a fluid medium, and more particularly, it pertains to a fluid analyzing detector which utilizes a sensor composed of a substance that changes in volume in the presence of the analyte to create a measurable pressure response in the detector.

2. Description of the Prior Art

Detectors for sensing the presence of an analyte, e.g., hydrocarbons, in a fluid mixture (gaseous or liquid) are well-known in the prior art. One typical prior art detector utilizes a generally solid substance which changes in volume (typically by expanding) in response to the intrusion of the particular analyte to be detected. This expansion of the detector substance can then be detected and (in some cases) measured to provide the appropriate output response.

For example, detectors which utilize a detector substance which swells in the presence of water to bend an optical fiber and thereby change the transmission characteristics in the fiber are shown in U.S. Pat. Nos. 4,596,443 to Diemeer et al and 5,430,815 to Shen et al.

When the analyte to be detected is a hydrocarbon fluid, e.g., gasoline or other hydrocarbon fuels, a detector substance such as red silicone rubber is used as the detector substance in a manner similar to that of the water or moisture detectors. For example, U.S. Pat. No. 5,378,559 to Lawrence illustrates a hydrocarbon detector which utilizes an expandable substance (red silicone rubber) to bend an optical fiber; U.S. Pat. No. 5,015,843 to Seitz et al, discloses a detector which utilizes a swellable polymer that shifts a reflector to change the light conductivity between a pair of fiber optic cables; U.S. Pat. No. 5,187,366 to Hopenfeld discloses a swellable substance in the presence of hydrocarbons which alter the light transmission through a fiber optic cable; and U.S. Pat. No. 4,590,462 to Moorehead discloses a hydrocarbon detector that utilizes a substance which expands to rotate a shaft and bend an optical fiber to measurably detect the presence of hydrocarbons.

Finally, U.S. Pat. No. 5,146,778 to Hsu discloses a detector for oil and/or water which utilizes a swellable material which upon exposure to the particular analyte raises a weighted signalling device that can be visually monitored.

A general problem with all of such prior art devices is their lack of sensitivity for detecting minute traces of an element, and more particularly, their general inability to accurately quantify the particular substance being detected.

SUMMARY OF THE INVENTION

With the present invention a fluid analyzing detector is provided for detecting the presence of an analyte (particularly hydrocarbon containing substances) in a fluid medium. In common with the prior art devices, the detector of the present invention utilizes a sensor material (such as red silicone rubber) which swells in the presence of hydrocarbons; however, in contrast with such prior art devices, the present invention utilizes a confined quantity of an incompressible liquid in pressure transmitting contact with the sensor material and a means for noting and accurately measuring the pressure response in the incompressible liquid when the analyte is present in the fluid medium that is directed to the sensor material.

In a specific modified version of the present invention, means can be provided to automatically compensate the output of the measuring means for changes in ambient conditions, i.e., temperature or atmospheric pressure.

The fluid analyzing detector of the present invention may be used to detect various analytes in various fluid environments, but it is particularly useful for sensing hydrocarbons in airborne gases or vapors. For example, the detector may be used to sense the presence of a methane gas as, for example, in detecting gas leaks emanating from natural gas lines. Also the detector may be used to sense gasoline vapors or benzene vapors in order to detect potentially hazardous situations as, for example, may exist in vehicles, buildings, sewers, etc.

With the choice of the appropriate sensor material, the present invention may also be used to sense and measure small quantities of water, a contaminant that may be present in fuels such as gasoline or diesel oil, etc.

BRIEF DESCRIPTION OF THE DRAWINGS

FIG. 1 is an exploded longitudinal section through the fluid analyzing detector of the present invention.

FIG. 2 is a side elevation, partially in section, of a second embodiment of the fluid analyzing detector of the present invention.

FIG. 3 is a side elevation, partially in section, of a third embodiment of the fluid analyzing detector of the present invention.

FIG. 4 is a side elevation, partially in section, of the fluid analyzing detector of FIG. 3 illustrating the device prior to the attachment of the piezoresistive pressure sensor.

FIG. 5, is a top plan view with portions thereof being broken away, of the fluid analyzing detector of FIG. 3.

FIG. 6 is an enlarged isometric view, with a portion thereof being broken away, of the top end of the fluid analyzing detector structure as shown in FIG. 4.

DESCRIPTION OF THE PREFERRED EMBODIMENTS

The basic fluid analyzing detector of the present invention is shown in exploded form in FIG. 1. Thus, a stainless steel cylinder 12 is provided which is closed at one end and which has throughout its length a plurality of perforations 13 extending through its wall, such perforations being of a sufficient size (e.g., 0.01 inches diameter) to readily admit gas or vapor to the interior of the cylinder body. A hydrocarbon sensitive material layer 14, such as red silicone rubber (RSR), is shaped so as to fit snugly within the cavity of the cylinder 12. The cylindrical body of the RSR is then filled with an incompressible liquid 16 such as water or silicone oil. Finally, the top of the cylinder is closed and sealed against the oil by a conventional piezoresistive pressure sensor 18 having electrical leads 19 which may be directed to a gauge or some other instrument to indicate a rise in the pressure within the cylinder.

In operation, air or common water vapor will have no effect upon the device. However, when a hydrocarbon gas or vapor passes through the perforations 13, the sensitive red silicone rubber 14 will expand to increase the pressure on the liquid fill 16 which increase in pressure is immediately detected by the pressure sensor 18 with the appropriate electrical signal thereby being provided by the electrical leads 19. Obviously, the liquid fill must occupy all of the entrapped space within the membrane-like walls of the red silicone rubber 14 and the enclosing pressure sensing device 18. Also, it is important to note that the rigidity of the cylinder 12 must be such that no outward flexing thererof occurs during the expansion of the hydrocarbon sensitive layer 14 so as to relieve the increased pressure on the liquid fill 16.

By adjusting the length of the body of the cylindrical detector 10, i.e., in the vertical direction as shown in FIG. 1, the sensitivity of the detector to various gases, such as methane, can be carefully controlled.

Also, instead of using a conventional pressure transducer 18 as previously described to measure the pressure response of the liquid fill 16, a "capacitance micrometer" as an integrated position sensor may be used to detect sub-nanometer movements of a semi-rigid sealing plate and thereby provide a very sensitive measure of the pressure increase in the incompressible liquid.

A second embodiment 20 of the invention is shown in FIG. 2, with this embodiment being provided with a visual pressure sensor as opposed to the electrical output signal type of pressure sensor used in the first described embodiment. Thus, detector 20 will be seen to be comprised of a cylindrical outer chamber 22 which may be formed of a sintered metal material that is permeable to liquids, gases and vapors but which will block solid particle intrusion. In the event that gases or vapors only are to be detected, the appropriate sintered metal material may be chosen so as to block liquid flow therethrough as well as solid particles. As with the prior embodiment, a red silicone rubber membrane 23 is provided about the interior chamber of the metal cylinder 22 so that hydrocarbon gases and/or liquids passing through the sintered metal material will be absorbed to cause the membrane 23 to attempt to expand inwardly. The enclosed interior of the membrane lined pocket in the cylinder 22 is filled with an incompressible fluid such as water 24 similar to the liquid fill 16 of the previously described embodiment. Finally, a capillary tube 26 is provided at the upper end of the cylinder 22 with such tube directly communicating with the liquid fill 24 as shown. The tube may by secured to the upper wall 22a of the cylinder and sealed from any leakage of the liquid fill by the red silicone rubber membrane 23 which encloses its lower end.

As shown in FIG. 2, the normal level of oil in the capillary tube 26 will be at a low level as indicated by the line 27 in FIG. 2. When the sensor material, i.e. the hydrocarbon sensitive membrane 23 expands inwardly the liquid fill in the capillary tube can be forced upward to some elevated level, as indicated by the dashed line 28 in FIG. 2, wherein it can be readily detected visually to indicate the presence of hydrocarbon gases filtering through the outer cylinder sintered metal 22. The relative concentration of such hydrocarbon gases can be determined by appropriately marked gradations along the length of the tube 26.

A third embodiment 30 of the invention is shown in FIGS. 3–6, this embodiment being provided with a means for automatically compensating for changes in ambient conditions, particularly temperature changes. While the simplified device 10 of FIG. 1 is useful for detecting the presence or absence of hydrocarbons or other analytes in the surrounding fluid medium and their general concentration level, it will be recognized that temperature variations will also cause changes in the pressurization of the liquid fill 16 to create varying output signals. Thus, the FIG. 1 device 10 would only accurately indicate the presence or absence of a hydrocarbon material and could only generally calibrate the precise amounts of such material present since absolute temperature values and the incremental changes thereof would affect the precise values read by the pressure sensor device.

In order to compensate for these variations in ambient conditions and as shown in FIG. 3, the stainless steel cylinder 32 of the detector 30 is relatively larger than the cylinder 12 of the first described embodiment and includes a solid (unperforated) center wall 33 extending the length thereof to provide two separate and isolated chambers 34 and 35 therewithin. Only a semi-cylindrical portion of the outer wall of the cylinder 32, i. e., that portion that surrounds the chamber 34, is provided with perforations 36 to readily admit the introduction of gas or vapor to the interior of such chamber. In contrast thereto, the wall of the cylinder 32 about the chamber 35 is solid and impervious to gas or vapor. As with the previously described embodiment, the semi-cylindrical walls of each of the chambers 34, 35 are aligned with a membrane-like sensor material 38 sensitive to hydrocarbons and subject to expansion in their presence, such material comprising red silicone rubber, for example. The remainder to the chambers 34, 35 within the silicone rubber walls can be filled with an incompressible liquid fill material 16 such as water or silicone oil as in the first described embodiment of the invention.

The upper end of the cylinder 32 is sealed with a dual or differential pressure sensor 40. As seen in FIGS. 5 and 6, the top of the cylinder can be sealed with a solid wall 42 provided with a pair of fittings 44 into which the probes 45 (FIG. 3) of the differential pressure sensor can be inserted and sealed. Electrical leads 46 and 47 may be provided for each of the separate pressure detecting elements of the dual pressure sensor 40 received atop the chambers 34 and 35. These will be directed to conventional circuitry (not shown) to provide an output signal which is compensated for pressure changes due to variations in ambient conditions.

The dual or differential pressure sensor 30 of FIG. 3 will thus be temperature compensated so that it will read absolute values of the amount of hydrocarbon presence in the ambient atmosphere. As the temperature rises, for example, and the pressure increases within each of the chambers 34 and 35, such pressure increase will be equal and no differential output signal will be provided by the sensor leads 46, 47. However, in the presence of a hydrocarbon vapor such as methane, the perforations 36 will allow entry through a portion of the cylinder wall to expand the red silicone rubber within chamber 34 while the solid wall about chamber 35 will prevent any such intrusion of hydrocarbons into the red silicone rubber within chamber 35. Thus, a differential pressure will exist between the chambers 34 and 35 only in the presence of hydrocarbons which is converted to an electrical output by the detector 30 with the appropriate differential output signal being provided by the lines 46, 47.

In practice, we have used a stainless steel cylinder having a wall thickness of about 25 millinches with a thickness of the red silicone rubber membrane layer being about 60 millinches. The perforations may be about 10 millinches and should take up at least 50% of the area of the cylinder in which they are placed.

Obviously, as an alternative to the perforated stainless steel cylinders of the FIG. 1 and FIG. 3 embodiments of the invention, a commercially available sintered metal filter material, such as that described with respect to the FIG. 2 embodiment of the invention, may be used instead.

While in each of the aforedescribed embodiments of the invention the incompressible liquid fill material 16 or 24 is in direct engagement with the inner surface of the sensor material layer 14, 23 or 38, such liquid fill material may be enclosed within a separate membrane, for example, so long as it is placed in pressure transmitting contact with the sensor material layer. This arrangement could prove useful or necessary when the sensor material is chemically incompatable with the liquid fill material or where the liquid fill material could flow into or through the sensor material.

Although the best modes contemplated for carrying out the present invention have been herein shown and described, it will be apparent that other modifications and variations may be made without departing from what is regarded to be the subject matter of the invention.

What is claimed is:

1. A fluid analyzing detector for detecting the presence and concentration of a particular analyte in a fluid medium, said detector comprising a sensor member of a material which changes in volume in the presence of said analyte in liquid or gaseous form, means for confining said sensor member in at least one direction while permitting the introduction of an analyte containing fluid substance thereto; a quantity of an incompressible liquid, means for confining said incompressible liquid in pressure transmitting contact with said sensor member, and means for sensing a pressure change in said incompressible liquid when the presence of an analyte containing fluid substance causes said sensor member to change the pressure exerted upon said incompressible liquid.

2. A fluid analyzing detector according to claim 1 wherein said sensor member is formed to provide an enclosed interior chamber, said interior chamber being filled with said incompressible liquid.

3. A fluid analyzing detector according to claim 1 wherein said means for sensing a pressure change comprises a pressure sensor in contact with said liquid to sense an increase in pressure thereto.

4. A fluid analyzing detector according to claim 1 wherein said means for sensing a pressure change comprises a capillary tube mounted to communicate with said liquid.

5. A fluid analyzing detector according to claim 1 wherein said means for confining said sensor member comprises a rigid member provided with a plurality of apertures about its periphery.

6. A fluid analyzing detector according to claim 1 wherein said means for confining said sensor member comprises a rigid member of a sintered metal material.

7. A fluid analyzing detector according to claim 1 wherein said sensor member comprises a membrane-like member having a relatively large dimensional area exposed to said analyte containing substance and a relatively small thickness dimension perpendicular to said area of exposure.

8. A fluid analyzing detector according to claim 1 including means for compensating for pressure responses in said incompressible liquid due to ambient conditions.

9. A fluid analyzing detector according to claim 8 wherein said compensating means comprises a second quantity of incompressible liquid, means for enclosing said second quantity of liquid within a predetermined space out of contact with said analyte containing fluid substance but subject to the same ambient conditions as the first mentioned quantity of liquid, means for measuring any pressure responses in said second quantity of liquid due to a change in ambient conditions, and means for adjusting the output of said means for sensing a pressure change in the first quantity of liquid in accordance with the output of said means for measuring pressure variations in the second quantity of liquid.

10. A fluid analyzing detector for hydrocarbon containing substances comprising a sensor member formed in the shape of a membrane and being comprised of a material which increases in volume in the presence of hydrocarbons in liquid or gaseous form, means for confining the outer surface of said sensor member while permitting the introduction of a hydrocarbon containing fluid substance over at least a portion of the outer surface area thereof, a quantity of an incompressible liquid, means for confining said incompressible liquid adjacent an inner surface area of the sensor member opposed to said portion of the outer surface area thereof so that the expansive force of the sensor member in the presence of hydrocarbons is transmitted to the incompressible liquid, and means for sensing a pressure increase in said incompressible liquid when the presence of a hydrocarbon containing fluid substance causes said sensor member to increase the pressure on said incompressible liquid.

11. A fluid analyzing detector according to claim 10 wherein said sensor member is formed to provide an enclosed interior chamber, said interior chamber being filled with said incompressible liquid.

12. A fluid analyzing detector according to claim 11 wherein said means for sensing a pressure increase comprises a pressure sensor in contact with said liquid within said interior chamber.

13. A fluid analyzing detector according to claim 11 wherein said means for sensing a pressure increase comprises a tube mounted to communicate with said interior chamber with said incompressible liquid extending from the chamber into a portion of the tube.

14. A fluid analyzing detector according to claim 11 wherein said means for confining said sensor member comprises a rigid member of generally cylindrical shape provided with a plurality of apertures about its periphery.

15. A fluid analyzing detector according to claim 12 wherein said means for confining said sensor member comprises a rigid member of a sintered metal material.

16. A fluid analyzing detector for detecting the presence and concentration of a particular analyte in a fluid medium, said detector comprising a quantity of an incompressible liquid, a sensor member of a material which changes in volume in the presence of said analyte in liquid or gaseous form, said sensor member being of a membrane-like shape and having inner and outer surfaces, said incompressible liquid being in pressure transmitting contact with at least a portion of the inner surface area of the sensor member, rigid means for completely confining said incompressible liquid and said sensor member so as to prevent any outward expansion of the sensor member, said rigid means including passages to permit the introduction of an analyte containing fluid substance to at least a portion of the outer surface area thereof, said inner surface area portion and said outer surface area portion being in generally opposed positions across the thickness of the membrane-like sensor member, and means for sensing a pressure change in said incompressible liquid when the presence of an analyte containing fluid substance causes said sensor member to change the pressure exerted upon said incompressible liquid.

17. A fluid analyzing detector according to claim 16 wherein said rigid means for confining is formed of a sintered metal material.

18. A fluid analyzing detector according to claim 16 wherein said inner surface area portion and said outer surface area portion of the sensor member comprise the major portions of such inner and outer surfaces.

* * * * *